US011016027B2

United States Patent
Stuart et al.

(10) Patent No.: US 11,016,027 B2
(45) Date of Patent: May 25, 2021

(54) METHODS FOR DETECTING FILM-FORMING AMINES IN WATER

(71) Applicant: CHEMTREAT INC., Glen Allen, VA (US)

(72) Inventors: Dale Stuart, Glen Allen, VA (US); Rajendra Prasad Kalakodimi, Glen Allen, VA (US)

(73) Assignee: CHEMTREAT, INC, Glen Allen, VA (US)

( * ) Notice: Subject to any disclaimer, the term of this patent is extended or adjusted under 35 U.S.C. 154(b) by 183 days.

(21) Appl. No.: 16/342,855

(22) PCT Filed: Jul. 30, 2018

(86) PCT No.: PCT/US2018/044331
§ 371 (c)(1),
(2) Date: Apr. 17, 2019

(87) PCT Pub. No.: WO2019/023699
PCT Pub. Date: Jan. 31, 2019

(65) Prior Publication Data
US 2019/0265165 A1    Aug. 29, 2019

Related U.S. Application Data

(60) Provisional application No. 62/538,487, filed on Jul. 28, 2017.

(51) Int. Cl.
*G01N 21/64* (2006.01)
*G01N 33/18* (2006.01)
(Continued)

(52) U.S. Cl.
CPC ............ *G01N 21/643* (2013.01); *C23F 11/00* (2013.01); *G01N 21/645* (2013.01);
(Continued)

(58) Field of Classification Search
CPC .. G01N 21/643; G01N 21/6428; G01N 21/77; G01N 21/645; G01N 33/18; G01N 2021/7786; C23F 11/00; C23F 11/141
See application file for complete search history.

(56) References Cited

U.S. PATENT DOCUMENTS

| 2012/0142113 A1* | 6/2012 | Banks | G01N 21/6428 436/43 |
| 2015/0260702 A1* | 9/2015 | Richardson | C02F 1/008 436/172 |
| 2016/0091469 A1* | 3/2016 | Lendi | G01N 21/253 436/85 |

FOREIGN PATENT DOCUMENTS

| EP | 0624798 A1 * | 11/1994 | G01N 33/1826 |
| WO | WO-2016203119 A1 * | 12/2016 | G01N 33/2835 |

OTHER PUBLICATIONS

Evtushenko, Yu M, et al., "Photometric Determination of Octadecylamine with Methyl Orange", 2002, Journal of Analytical Chemistry, vol. 57 (1), pp. 8-11. (Year: 2002).*
(Continued)

*Primary Examiner* — Jill A Warden
*Assistant Examiner* — Henry H Nguyen
(74) *Attorney, Agent, or Firm* — Oliff PLC

(57) ABSTRACT

Methods and systems for detecting and quantifying film forming amines in water systems are described. Water containing a film forming amine is combined with a fluorescent dye, the pH of the water is reduced, and then the fluorescence signal of the fluorescent dye is measured. The fluorescence signal is indicative of the amount of film forming amine in the water, and can be used to quantify the amount of film forming amine and control the amount of film forming amine that is introduced into the water system.

13 Claims, 3 Drawing Sheets

(51) Int. Cl.
*G01N 21/77* (2006.01)
*C23F 11/14* (2006.01)
*C23F 11/00* (2006.01)

(52) U.S. Cl.
CPC ......... *G01N 21/6428* (2013.01); *G01N 21/77* (2013.01); *G01N 33/18* (2013.01); *C23F 11/141* (2013.01); *G01N 2021/7786* (2013.01)

(56) References Cited

OTHER PUBLICATIONS

Fu, Yanayan, et al., "A BODIPY dye as a reactive chromophoric/fluorogenic probe for selective and quick detection of vapors of secondary amines," Oct. 2013, Chem. Commun., 49, 11266-11268. (Year: 2013).*
Translation of Hurtevent, Christian, Dec. 22, 2016, WO 2016203119 A1 (Year: 2016).*
Chemtex, "Neutralizing Amine Regulation &Testing", Feb. 16, 2010, International Chemtex Corporation, pp. 1-2 (Year: 2010).*

* cited by examiner

METHODS FOR DETECTING FILM-FORMING AMINES IN WATER

BACKGROUND

Film-forming amines ("FFA") are used to inhibit corrosion in industrial water systems for boiler water, steam treatments, and other high temperature corrosive environments. FFAs are particularly useful in water systems where it is desired to inhibit corrosion in a condensate system because the FFAs are somewhat volatile and can be transferred from the liquid to vapor state with steam. The FFA can provide corrosion protection when the steam is condensed on equipment surfaces of the water system.

By way of example, boilers generate power by elevating water temperature while limiting the escape of the steam, which generates higher pressure that further increases the boiling point of the water. Most boilers are made of mild steel, which requires an elevated pH to inhibit corrosion. The elevation of pH creates a faster oxidation of the ferrous hydroxide evolving from the mild steel matrix in the anode. The lower solubility of the ferric hydroxide and the higher concentration around the anode create a system where ferric and ferrous hydroxide combine to create magnetite. This magnetite layer creates a membrane over the anode that prevents the escape of the ferrous ion, and therefore, inhibits corrosion. However, adding sodium hydroxide by itself to elevate pH frequently results in sodium building up underneath the membrane, which causes a special type of corrosion called caustic hideout that results in decarborization and subsequent generation of methane pockets within the iron matrix. To prevent caustic hideout, sodium is added to phosphoric acid to generate a sodium to phosphate molar ratio that targets the elevated pH needed for boiler to maintain safe operation.

After the water is heated in the boiler, the steam leaves the boiler through a condensate system that directs the steam to the areas where work is performed. The condensate system piping is frequently made of mild steel while heat exchange surfaces typically are made of either aluminum, copper, or mild steel. Turbines am frequently made of titanium or an alloy containing titanium. Amines or ammonia are typically added to the condensate system to elevate the pH of the system. The amines have a liquid to vapor distribution so that some amine is imparted into the condensing water phase thereby elevating the pH. This inhibits corrosion in a similar fashion as the sodium phosphate docs in the boiler. Boiler systems used for power generation can be used to generate power on a consistent basis or for peak conditions. For boiler systems generating power for peak conditions, the boiler runs only for a specific time period when the peak power is needed and then shuts down. The water in the boiler is maintained at a relevant pH through maintaining the correct sodium to phosphate ratio and circulating the water in the boiler. However, the ability to elevate the pH of the condensate system through the application of amines/ammonia is lost because these treatments are injected into the steam and subsequently circulated with the steam and steam circulation is not present when the boiler system is shutdown.

The application of FFAs such as octadecyl amine, oleyleamine, or N-olyelpropane-1,3-diamine can create a barrier along the metal in the condensate circuit dial prevents the escape of the corrosion byproducts, decreases the solubility of dissolving iron, and thereby inhibits corrosion. FFAs should be added to the water system so that enough of the material residual is present in the system to develop the film. The filming amine has a surfactant-type structure and is sparingly soluble so the filming amine is applied in the water system (e.g., boiler water or steam header) such that a small residual is detected in the condensate receiver. This ensures that all components of the condensate system have been exposed to the filming amine.

Since film forming amines are sparingly soluble, the micelles formed at higher concentrations will aggregate in flow restricted areas of the condensate system. This evolving mass will grow and further restrict flow. This flow restriction cart cause system disruptions that are unsafe and can be troublesome to clean. To prevent this from happening, it is desirable to apply the filming amine in high enough concentration to ensure a film is covering the system but low enough not cause systemic flow problems. To successfully treat a system with filming amine, it is desirable to be able to detect the residual of filming amine in the system.

One field method to detect filming amines uses a Bengal rose dye and a buffer. The final solution pH needs to be between 2.3 and 3.3 with the maximum response given at pH=2.6. However, there are significant problems adjusting pH within this range to get a precise response, and the assay is generally not considered to be robust or reproducible. Thus, boiler operators and other water treatment field representatives do not prefer this technique despite the advantages of detecting film forming amine (FFA) concentration to ensure protection and prevention of FFA overfeed.

Another method uses derivatization of FFA with ortho pthalaldehyde to improve fluorescent detection in high-performance liquid chromatography (HPLC). However, HPLC instruments are significant in stature and need laboratory grade eluents, which preclude its use for field applications as are necessary for onsite analysis of FFA residuals to ensure proper application is followed.

SUMMARY

Maintaining a proper residual of filming amine can significantly affect the operation of the water system, such as a boiler. Feeding loo little may cause severe corrosion due to the lack of corrosion inhibition. This could cause shut down of the plants and/or personnel safety issues. Overfeeding of the filming amine can also be bad for the system. Many times, the filming amines are blended with a neutralizing amine for stability reasons and overfeeding the filming amine will ultimately lead in overfeeding of the neutralizing amine. This will lead to increased pH of the condensate and cause severe corrosion an copper alloys. Hence, an accurate method of measuring the residual of the filming amine is extremely critical to the safe operation of the boilers. This disclosure provides accurate and convenient methods for measuring residual filming amine concentration.

In one aspect, the invention provides a method of detecting and quantifying film forming amines in water systems. Water containing the film forming amine is combined with a fluorescent dye, the pH of the water is reduced, and then the fluorescence signal of the fluorescent dye is measured. The film forming amine can be quantified because the intensity of the fluorescence signal is indicative of the amount of film forming amine in the water. In some aspects, the determined amount of film forming amine can be compared to a target amount, which in turn can be used control the amount of film forming amine that is introduced into the water system.

DETAILED DESCRIPTION OF EMBODIMENTS

Figure 1:
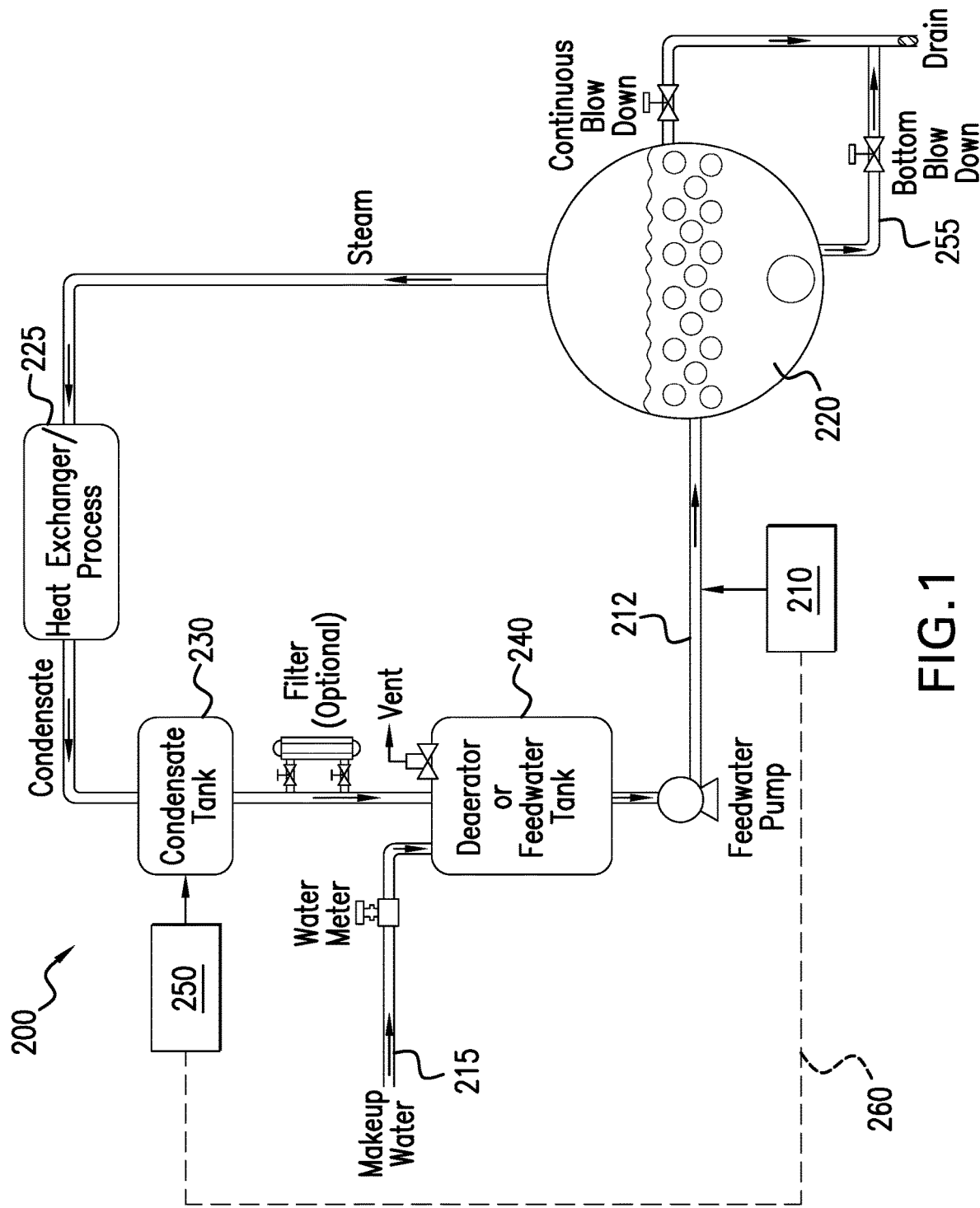
FIG. 1 is a schematic diagram illustrating a boiler system.

This disclosure describes a test for filming forming amines ("FFAs") that is more accurate than currently-used assays and can quickly and conveniently be used onsite in water systems. In one aspect, the method includes sampling a known volume of process water treated with an FFA, adding an acidic buffer and fluorescent dye to the sample, and measuring a fluorescence signal. The methods and systems described herein can detect and quantify FFAs that are used for corrosion inhibition in water systems.

Suitable FFAs that can be detected and quantified according to the methods and systems described herein may include, for example, higher molecular weight amines with a surfactant type structure. The hydrocarbon group of the amine may be straight chained, branched, saturated or unsaturated, substituted or unsubstituted. The hydrocarbon group can include 5 to 40 carbon atoms, 10 to 30 carbon atoms, or 15 to 25 carbon atoms. The FFA can include at least one primary amine group. The FFA may have a molar mass in the range of 150 to 400 g/mol, from 200 to 350 g/mol, or from 225 to 300 g/mol. Suitable FFAs may include octadecyl amine, oleyleamine, N-olyelpropane-1,3-diamine, or combinations thereof.

A fluorescent dye is added to a sample of the water which contains the FFA. The dye should associate with FFA to form an FPA/dye complex that affects the fluorescent signal of the dye. For example, the dye may selectively associate with primary amine groups, which reduces the fluorescent emission signal of the fluorescent dye. The fluorescent dye can be an anionic fluorescent dye. Examples of suitable fluorescent dyes may include Fluorescein, Sulforhodamine B, 5-carboxy-x-rhodamine, 6-carboxy-x-rhodamine, Naphthofluorescein, 2-(p-Tolyl)benzoxazole, Sulforhodamine 101 acid chloride, 5(6)-Carboxy-2',7'-dichloro fluorescein, 9-(2-Carboxyphenyl)-6-dimethylamino-3-xanthenone sulfate, Anthracene-1-sulfonate, 9,10-dioxo-9,10-dihydro-anthracene-1-sulfonate, Anthracene-2-sulfonate, 5,10,15,20-Tetrakis (1-methyl-4-pyridinio) porphyrin tetra (toluene-4-sulfonate), 6-Hydroxy-2-naphthyl disulfide, 5(6)-Carboxy-2',7'-dichloro fluorescein diacetate, 2-naphthalenesulfonic acid, 1,3,6,8-Pyrenetetrasulfonic acid (PTSA), and combinations thereof. The dye may be added to the sample so that it is present in a concentration in the range of from, for example, 0.1 to 10 ppm, 0.2 to 5 ppm, 0.3 to 2 ppm, 0.4 to 1 ppm, and 0.1 to 0.5 ppm.

In measuring the FFAs according to this disclosure, an acid or acidic buffer is also added to the sample to depress the pH and maintain a pH that is sufficient for the FFA to develop a positive charge. The acid or buffer can be added separately or together with the dye as a mixture. Before the acid or buffer is added, the water typically has a pH that is in the range of 8 to 11, 8.5 to 10.5, or 9 to 10, for example. The acid or buffer can reduce the pH of the water sample to a pH that is at least 1 pH unit below the pKa of the film forming amine, at least 1.5 pH unit below the pKa, at least 2 pH units below the pKa or from 2 to 4 pH units below the pKa. The pH of the sample after the acid or buffer is added can be in the range of 4-7, 5-7, or 6-7. The acid can be any suitable acid that will lower the pH of the sample to the desired level, e.g., phosphoric acid, hydrochloric acid, hydrofluoric acid, etc. In most applications, it is most convenient to use an acidic buffer to more stably control the pH of the sample. The buffer can be any suitable buffer that will depress the pH of the sample, including monosodium phosphate, sodium hydrogen phthalate, partially neutralized citric acid, partially neutralized acetic acid, and combinations thereof. The buffer can be added to the sample so that it is present in a concentration in the range of, for example, 50-1,000 ppm, 80-500 ppm, 100-250 ppm, and 150 to 200 ppm.

If the dye and buffer are added to the water as a mixture, a volume of the mixture can be added to a larger volume of the water. The dye may be present in the reagent mixture in amounts of, for example, from 10 ppm to 1,000 ppm, from 20 ppm to 500 ppm, from 30 ppm to 200 ppm, and 40 ppm to 100 ppm. The buffer can be present in the reagent mixture in amounts of, for example, from 5,000 to 100,000 ppm, 8,000 to 50,000 ppm, 10,000 to 25,000 ppm, and 15,000 to 20,000 ppm.

The dye/FFA complex that is formed in the sample may be somewhat unstable in that the dye and FFA can become disassociated with each other and thus the effect of the FFA on the fluorescent signal is diminished over time. Specifically, the depression in pH can create an attraction between the dye and the filming amine, however, the dye complex can take time to form and may fall apart quickly. The fluorescent dye and FFA that are used may have a characteristic period where the complex is most stable (see, e.g., FIG. 5, discussed below). More accurate results can be obtained by measuring the fluorescent signal within the characteristic stability period, e.g., where the fluorescent signal does not change by more than 5% over a one-minute period, and preferably does not change by more than 2% or by more than 1% over a one-minute period. The characteristic stability period may occur in a range of, for example, 1 to 10 minutes after adding the dye/buffer to the sample, from 2 to 8 minutes, or from 3 to 5 minutes. Thus, reproducible results can be achieved by ensuring the pH Is depressed sufficiently and noting the time that the complex is allowed to develop so that the effect of the FFA on the fluorescence signal correlates in a substantially linear fashion to the concentration of FFA. Thus, in one aspect, once sufficient dye and butter has been added to depress the sample pH to the target level, it may be desirable to wait for the FPA/dye complex to develop and reach a characteristic stability period before raising a fluorescent reading.

Using the methods described herein, the FFA/dye complex typically results in a drop in fluorescence signal that is substantially proportional to the amount of FFA. This allows the amount of FFA in the sample to be detected and quantified. One way to quantify the amount of FFA in the water is by comparing the fluorescence signal response to a using a predetermined standard curve that compares the intensity of the signal at a certain wavelength to known concentrations of the FFA.

The standard curve can be prepared using set concentrations of dye/buffer and varying concentrations of the FFA. The curve should preferably, though not necessarily, be linear at expected concentrations of FFA, which allows for a simple and reliable calculation of the FFA concentration. For example, to determine the standard curve, the fluorescent signals of the dye in the presence of various known concentrations of FFA are measured at the wavelengths at which the fluorescent dye exhibits peak (or close thereto) excitation and/or emission. The intensities of the signals are plotted against the concentration of FFA, and a regression of these data points is performed. The type and amounts of dye and buffer and the development time (as explained above) are preferably selected such that, for the desired range of detectable FFA detection, the regression yields a linear relationship that closely matches the data points (i.e., the $R^2$ value is preferably near 1, e.g., more than 0.99, although in practice lower $R^2$ coefficients such as more than 0.85, 0.9, 0.95, or 0.97 may be suitable).

In applications where film forming amines are used, it is frequently desired to also add neutralizing amines (also called "alkalizing amines") to the water to increase the pH. A higher pH prevents the formation of carbonic acid from carbon dioxide in air, which itself can attack equipment. Typical neutralizing amines are lower molecular weight amines such morpholine, cyclohexylamine, diethylethanol amine, and methoxypropyl amine. The neutralizing amines can be present in the water in amounts of, for example, from 0.5 to 50 ppm, from 1 to 30 ppm, from 5 to 25 ppm, and from 10 to 20 ppm. Advantageously, the methods described herein can accurately quantify the amount of FFA without substantial interference from the presence of neutralizing amines, even though many of the neutralizing amines include a primary amine. Without intending to be bound by theory, it is believed that the larger hydrocarbon group on the FFA dampens the fluorescence signal of the dye, whereas smaller hydrocarbon groups, as are typical in neutralizing amines, do not have a significant effect on the fluorescence signal response.

The measured amount of FFA corresponds to the amount of residual FFA in the water system, i.e., the FFA that is present in the water and not present as a film on equipment surfaces. The measured amount of residual FFA can then be compared to the expected or desired amount. For example, to ensure that sufficient FFA is present in the water system so that a protective film is formed on the equipment surface, it is desirable that at least some residual FFA is present in the water. For cost and other reasons (e.g., aggregation and flow restriction, as discussed above), it may also be desirable that the residual FFA docs not exceed a threshold amount. For example, the target or desired residual FFA amount may be in the range of, for example, from 0.05 to 20 ppm, from 0.1 to 10 ppm, from 0.15 to 5 ppm, and from 0.2 to 1 ppm.

Based on the information obtained from the assay, the amount of FFA in the water system can be controlled by (a) determining the concentration of FFA according to the techniques described above, (b) comparing the concentration of FFA to a minimum or maximum threshold level, or to a predetermined desired concentration range; (c) adjusting the concentration of FFA if the concentration is not within the desired range, e.g., by adding more or less of the FFA; and (d) repeating the above process until the concentration of FFA is determined to be within the desired concentration range.

In the methods and systems according to aspects of this disclosure, the concentration of FFA can be determined and controlled regularly and/or automatically. In practice, samples can be periodically taken from the water system, and a bench top fluorometer or a handheld fluorometer may be used to measure the fluorescein signal. The sampling and assay can be automated, e.g., with an automate insipient analyzer, where a sampler periodically grabs samples, adds the dye/buffer reagent, and measures the fluorescence signal. Alternatively, each of these steps can be manually performed. Computer hardware (e.g., processor, memory, display) and software can be used to automatically record the measured fluorescence signals and to compare the measured signals to a stored standard curve to determine the amount of FFA. The calculated amount of FFA can be then be compared to a stored desired FFA concentration range the data can be logged into a database, plotted, and displayed and evaluated by an operator. The computer hardware and software may be configured as feedback control that sends signals to an FFA feed pump that controls the introduction of FFA into the water system. The pump can be a 4 to 20 mA adjustable feed pump or can be controlled by an on/off boost base method to obtain the targeted FFA residual.

The methods described herein are useful in any water systems where an FFA is used. The water system may be, for example, an industrial water systems such as steam generating systems, boilers, condensate systems, cooling water systems, cooling towers, surface condensers, scrubbers, heat exchangers, air washers, evaporative condensers, once-through cooling water systems, paper mill water systems, reverse osmosis system feedwater, brewery pasteurizers and the like.

The methods according to one aspect of this disclosure are described in FIG. 1 in connection with a boiler system 200. Corrosion is a problem caused by water in the boiler. Corrosion can be caused by dissolved oxygen, corrosion currents due to heterogeneities on metal surfaces, or by the water directly attacking iron in the boiler. Corrosion may occur in the feed-water stream as a result of low pH water and the presence of dissolved oxygen and carbon dioxide. Corrosion is also a problem in the condensate return, which is typically composed of mild steel piping and equipment, and occasionally copper alloys. Corrosion in the condensate system is often in the form of pitting which can cause failure of the equipment if not monitored.

FIG. 1 illustrates a typical boiler system 200, where the boiler 220 heats water to provide steam for a heat exchanger 225 or other process. Condensate from the heat exchanger is collected in a condensate tank 230 that is fed to a deaerator or feedwater tank 240 before being directed back to the boiler 220. The deaerator can remove oxygen and carbon dioxide to low levels in the boiler feedwater. Makeup water stream 215 is directed to tank 240 as needed to ensure that the amount of water in the system remains constant. The make water stream can be metered into tank 240 with a water meter that can be controlled based on, e.g., a water level sensor in fire boiler. The boiler also has a continuous and bottom blow down 255 to remove water from the boiler.

The FFA can be introduced at port 210 into the return water stream 212 where the FFA is pumped as needed to provide adequate corrosion protection in the system. The FFA could similarly be supplied directly to the boiler water or to the makeup water stream 215. FFAs are typically volatile long-chain amines that attach themselves to metal in an invisible monomolecular layer, which imparts strong water repellence to the surface of the metal. The water repellence makes steam condense in droplets, which boosts heat transfer rates over those obtained when the steam condenses filmwise. The FFAs vaporize along with the steam and then condense with the steam together with any dissolved CO2. As the amine and CO2 dissolve in the condensate, the resulting solution becomes alkaline and noncorrosive to carbon steel. The water system may also include other chemicals to prevent corrosion or control pH such as a chemical oxygen scavenger in the boiler water or ammonia in the condensate.

To determine the residual concentration of FFA, water from the condensate tank 250 can be sampled and assayed at monitoring station 250 using the methods described above. The monitoring station 250 may communicate with a pump or valve of port 210 via feedback control loop 260 to control the amount of FFA that is introduced to the boiler based on the results from monitoring station 250.

EXAMPLES

The following examples of the assay described herein were performed using N-olylpropane-1,3-diamine as the FFA, PTSA as the fluorescent dye, and sodium phosphate dibasic (NaH2PO4) as the buffer.

The sample procedures include (i) adding 1.0 ml of reagent including fluorescent dye and buffer to 100 ml sample of water that includes the FFA, (ii) mixing the sample and decanting it into a fluorometer cuvette, (iii) allowing minutes to pass for the dye/FFA complex to stabilize, and (iv) measuring the fluorescence emission at a wavelength of 405 nm.

Figure 2:
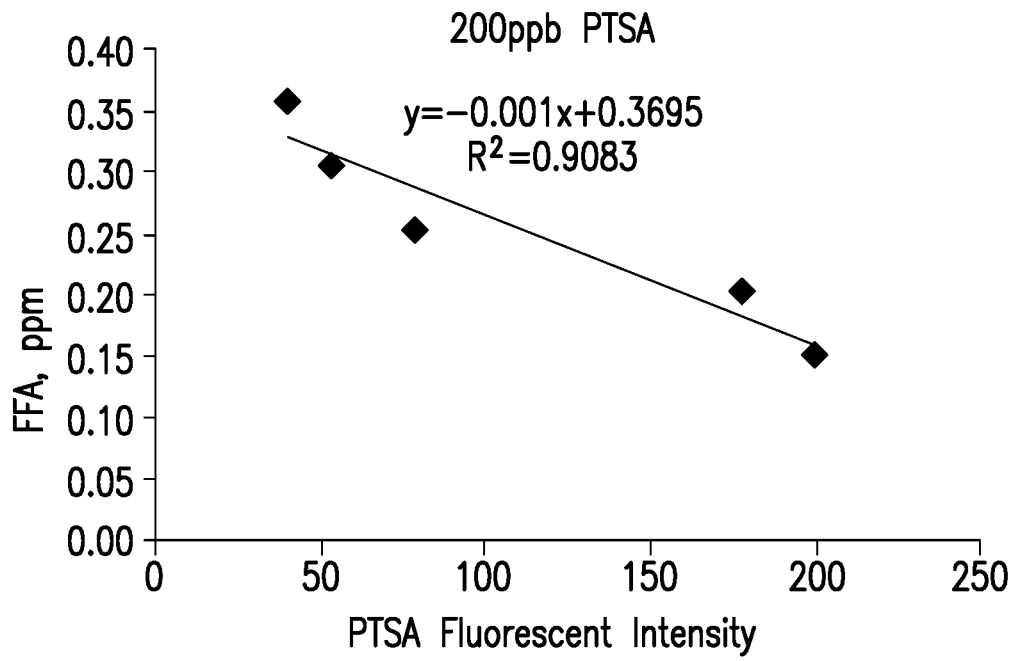
FIGS. 2-4 are graphs showing the fluorescence intensity of PTSA at varying concentrations of FFA.
Figure 3:
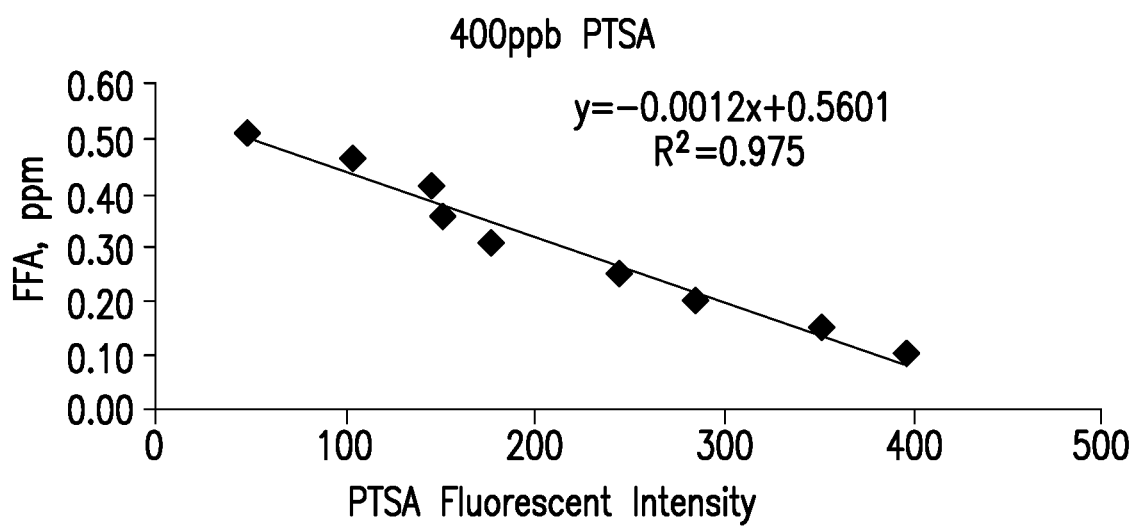
Figure 4:
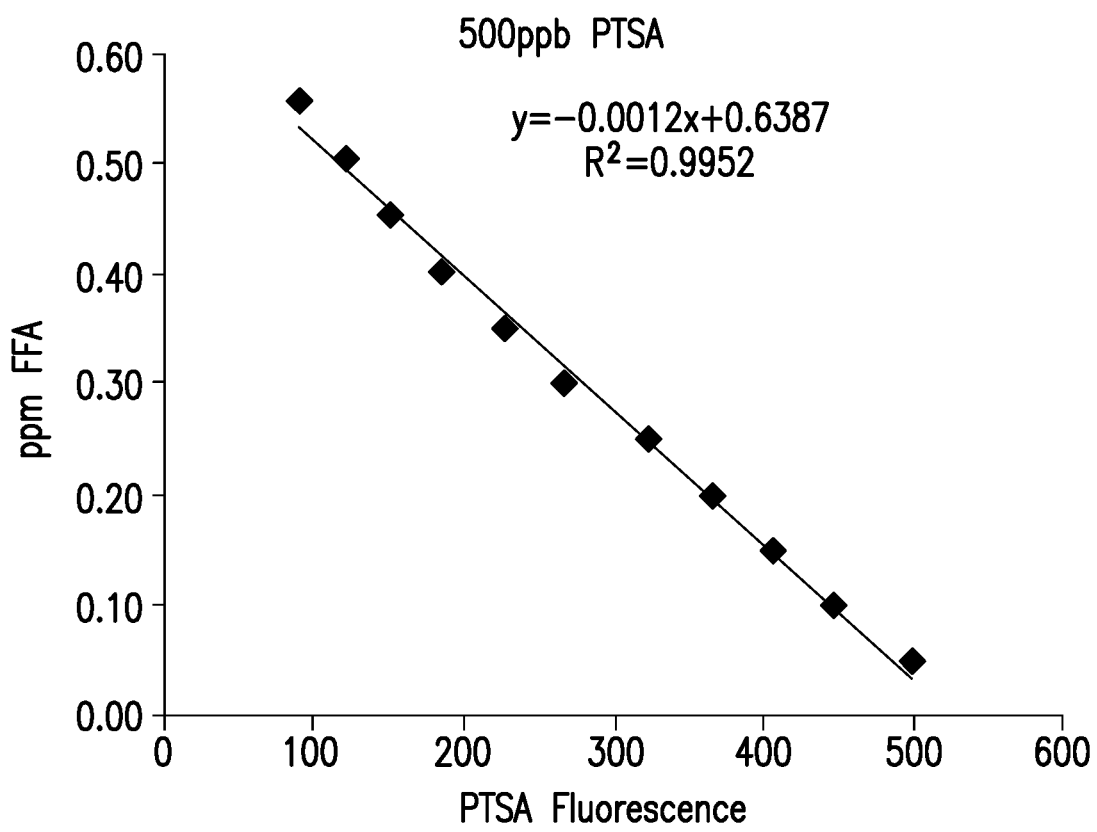

FIGS. 2-4 are graphs slowing data in which the PTSA fluorescent intensity signal is measured at known concentrations of FFA. The FIG. 2 example uses a concentration of PTSA of 200 ppb in the water sample, the FIG. 3 example uses a PTSA concentration of 400 ppb, and the FIG. 4 example uses a PTSA concentration of 500 ppb. Each of these examples uses a buffer concentration of 80.4 ppm monosodium phosphate in the sample.

Each of FIGS. 2-4 show a linear response of the PTSA fluorescent intensity to the concentration of FFA, which should allow the FFA concentration in water samples to be accurately measured. As can be seen, using 500 ppb of PTSA is associated with the best $R^2$ value, and can detect the widest range of FFA (0.05 to 0.55 ppm).

Figure 5:
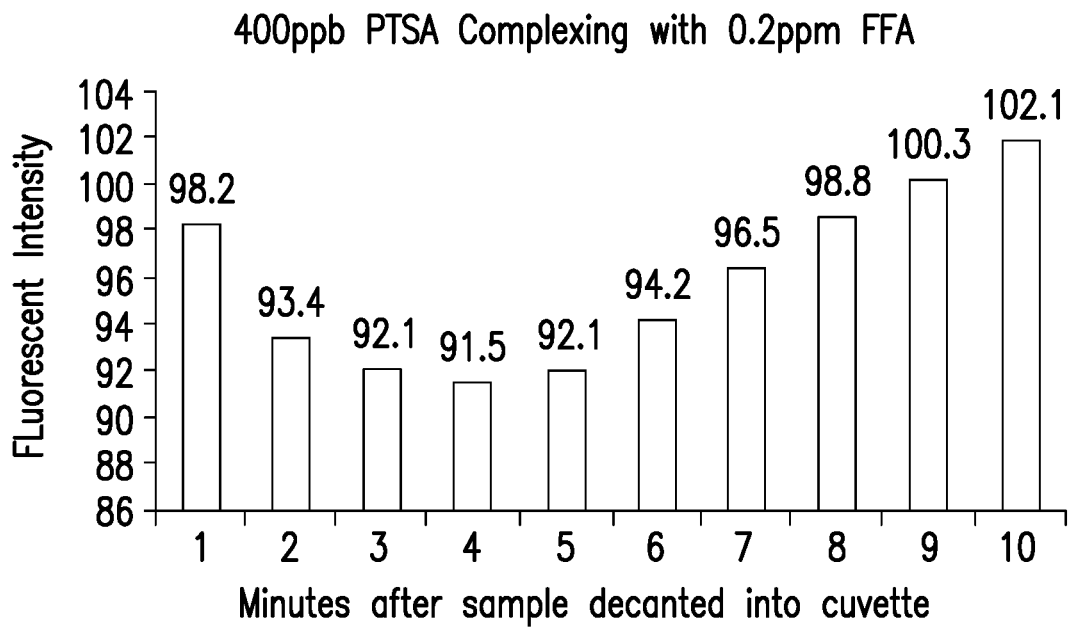
FIG. 5 is a graph showing the stability of the PTSA fluorescence intensity over time.

FIG. 5 is a graph show ng the stability of the PTSA-FFA complex. In the FIG. 5 data, fluorescent readings were taken at one-minute intervals after combining the buffer/PTSA reagent with the water sample. A PTSA concentration of 400 ppb in the water sample was used, and a buffer concentration of 80.4 ppm was used.

As can be seen the PTSA-FFA complex exhibits a characteristic stability period that is most stable between 3 and 5 minutes. In this regard, the fluorescent intensity readings vary by less than 1% in this timeframe. Thus, for reproducibility of results, it is desirable to take the fluorescent readings at a specified time within this range.

To check the precision and accuracy of the assay, five identical assays were performed using 0.3 ml of FFA, a buffer concentration of 80.4 ppm monosodium phosphate in the sample, and a PTSA concentration of 500 ppb in the sample. The observed PTSA signal and the amount of calculated FFA based on the observed signal is determined according to the standard curve shown in FIG. 4. The results are shown in Table 1 below.

TABLE 1

| Test# | ml FFA | PTSA Intensity ppb | calculated FFA, ppm |
|---|---|---|---|
| 1 | 0.3 | 252.3 | 0.33594 |
| 2 | 0.3 | 257.9 | 0.32922 |
| 3 | 0.3 | 253.3 | 0.33474 |
| 4 | 0.3 | 251.4 | 0.33702 |
| 5 | 0.3 | 254 | 0.339 |
| Average | | 253.78 | 0.334164 |
| STD DEV | | 2.505391 | 0.003006473 |

Statistical analysis using a t-test was then performed on the data. The results of this analysis are shown in Table 2 below.

TABLE 2

| 90% CL factor | 2.13 | 2.13 |
|---|---|---|
| 90% CL interval | 2.386551 | 0.002863861 |
| 90% CL Min | 251.3934 | 0.331300139 |
| 90% CL Max | 256.1666 | 0.337027861 |

Statistical analysis using the t-test indicates 0.3 ppm FFA would detect on average 0.334 ppm FFA with a range of 0.331 to 0.337 ppm FFA using a 90% confidence limit. Additionally, the test shows 0.03 ppm more FFA than was used for the test so there is a slight bias to a higher reading but this would round to 0.3 ppm when considering the significant figures used to determine the test. The level of precision and reproducibility would be considered acceptable for field use and a significant improvement over currently used methods.

Next, the FFA detection assay was performed in the presence of various neutralizing amines to determine whether the neutralizing amines interfered with the test results. Tables 3-6 respectively show the test results using different amounts of morpholine, cyclohexamine, diethylethanolamine (DEAE), and methoxypropyl amine (MOPA). Each assay employed 0.3 ppm of FFA and 160.8 ppm NaH2PO4 buffer. The measured FFA was calculated based on the observed PTSA signal.

TABLE 3

| morpholine, ppm | ppm FFA | PTSA | calculated FFA |
|---|---|---|---|
| 26.3 | 0.3 | 295.2 | 0.28446 |
| 13.1 | 0.3 | 283.2 | 0.29886 |
| 6.57 | 0.3 | 265.8 | 0.31974 |
| 26.3 | 0.3 | 279.7 | 0.30306 |

TABLE 4

| Cyclohexylamine, ppm | ppm FFA | PTSA ppb | calculated FFA |
|---|---|---|---|
| 26.4 | 0.3 | 313.6 | 0.26238 |
| 13.2 | 0.3 | 301.1 | 0.27738 |
| 26.4 | 0.3 | 276 | 0.3075 |

TABLE 5

| DEAE, ppm | ppm FFA | PTSA | calculated FFA |
|---|---|---|---|
| 25.6 | 0.3 | 265.8 | 0.31974 |

TABLE 6

| MOPA, ppm | ppm FFA | PTSA | calculated FFA |
|---|---|---|---|
| 25.6 | 0.3 | 284.5 | 0.2973 |
| 0 | 0.3 | 248 | 0.3411 |

As can be seen by Tables 3-6, even at very high levels of neutralizing amine (e.g., 25 ppm), the assay is sufficiently reproducible that the amount of residual FFA can be determined with reasonable accuracy.

The amount of buffer affects the interference by the neutralizing amines. Tests where less buffer was used (e.g., 80.4 ppm) showed that the neutralizing amines tended to exhibit more interference.

It will be appreciated that the above-disclosed features and functions, or alternatives thereof, may be desirably combined into different systems or methods. Also, various alternatives, modifications, variations or improvements may be subsequently made by those skilled in the art. As such, various changes may be made without departing from the spirit and scope of this disclosure.

What is claimed is:

1. A method of detecting film forming amine that is present in water, the method comprising (i) combining the water, an anionic fluorescent dye, and at least one of an acidic buffer and an acid, and (ii) then measuring a fluorescence signal of the fluorescent dye, wherein the film forming amine includes at least one primary amine group that associates with the anionic fluorescent dye and wherein the primary amine group associates with the anionic fluorescent dye, which reduces the fluorescent emission signal of the anionic fluorescent dye.

2. The method of claim 1, further comprising determining the amount of film forming amine in the water based on the measured fluorescence signal.

3. The method of claim 1, wherein the film forming amine is present in the water in an amount that is in the range of 0.05 ppm to 20 ppm.

4. The method of claim 1, wherein the acidic buffer is combined in sufficient amounts with the water so that the pH of the water is in the range of 4 to 7.

5. The method of claim 1, wherein the water further includes a neutralizing amine.

6. The method of claim 5, wherein the neutralizing amine is present in the water in an amount that is in the range of from 1 to 30 ppm.

7. The method of claim 1, wherein the acidic buffer is combined so that is present at a concentration in the range of from 80-500 ppm.

8. The method of claim 1, wherein the anionic fluorescent dye is 1,3,6,8-Pyrenetetrasulfonic acid and the fluorescent signal is measured between 3 and 5 minutes from the combining step.

9. The method of claim 1, wherein the anionic fluorescent dye and the acidic buffer are added to the water as a mixture.

10. A method comprising: (i) combining water that contains a film forming amine with an anionic fluorescent dye; (ii) reducing the pH of the water; and (iii) then measuring a fluorescent signal of the fluorescent dye, wherein the film forming amine includes at least one primary amine group that associates with the anionic fluorescent dye and wherein the primary amine group associates with the anionic fluorescent dye, which reduces the fluorescent emission signal of the anionic fluorescent dye.

11. The method of claim 10, wherein the pH of the water is reduced by combining the water with an acidic buffer.

12. The method of claim 10, wherein the pH of the water is reduced to a pH that is at least 2 pH values below the pKa of the film forming amine.

13. The method of claim 1, wherein the film forming amine includes a hydrocarbon group with 5 to 40 carbon atoms.

* * * * *